United States Patent [19]
Lim et al.

[11] Patent Number: 5,420,362
[45] Date of Patent: May 30, 1995

[54] SYNTHESIS OF 2-METHYL-1-NAPHTHOL

[75] Inventors: Mu-Ill Lim, Trumbull; Linas Stasaitis, Fairfield; Yuo-Guo Pan, Stamford, all of Conn.; Alexander Chan, Mineola, N.Y.

[73] Assignee: Clairol, Inc., New York, N.Y.

[21] Appl. No.: 133,352

[22] Filed: Oct. 8, 1993

[51] Int. Cl.⁶ ............................................. C07C 39/14
[52] U.S. Cl. ................................. 568/736; 568/735; 568/737; 568/739; 568/740
[58] Field of Search ............... 568/739, 740, 736, 735, 568/737

[56] References Cited

U.S. PATENT DOCUMENTS

| | | | |
|---|---|---|---|
| 3,919,332 | 11/1975 | Wollensak | 568/736 |
| 3,993,701 | 11/1976 | Leach et al. | 568/736 |
| 5,278,343 | 1/1994 | Taniura et al. | 568/736 |

*Primary Examiner*—Werren B. Lone
*Attorney, Agent, or Firm*—Morton S. Simon

[57] ABSTRACT

4-Halo-1-naphthol is reacted with a secondary amine and formaldehyde to produce a reaction mixture containing a Mannich base which is hydrogenated to produce 2-methyl-1-naphthol. Advantageously, the procedure can be carried out in one pot.

10 Claims, No Drawings

SYNTHESIS OF 2-METHYL-1-NAPHTHOL

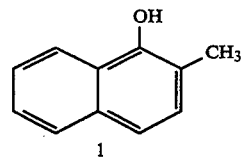

2-methyl-1-naphthol is very useful as a coupler in permanent hair coloring. It couples with p-aminophenol and with p-aminophenol derivatives to impart a bright red coloration to hair. Although 2-methyl-1-naphthol is commercially available from Aldrich Chemical Company, it is too expensive to use as a hair colorant. Consequently, there is great need for a convenient and economical method for producing 2-methyl-1-naphthol, so that the cost of 2-methyl-1-naphthol is reduced and greater use can be made of it in hair dye processes.

BACKGROUND OF THE INVENTION

Numerous processes are known for the synthesis of 2-methyl-1-naphthol.

Watanabe et al (Chem. Pharm. Bull., 37 (9) 2564–2566, 1989) teach a synthesis which may be depicted as follows:

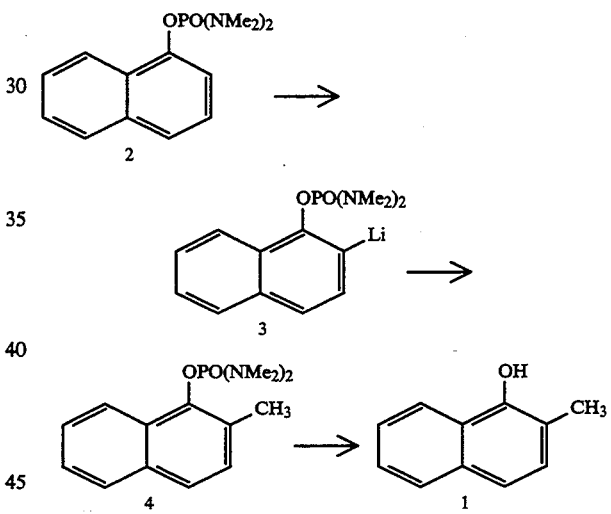

1-naphthol (5) was heated with twice its weight of $KHCO_3$ at 200° C. for 5 hours (stainless steel bomb) whereby 1-hydroxy-2-naphthoic acid (9) was obtained in a yield of 60%. 1-Hydroxy-2-naphthoic acid (9) was treated with methyl chloroformate and triethylamine in THF, followed by sodium borohydride reduction, whereby 2-methyl-naphthol (I) was produced in a yield of 80%.

Anon. (USA) (Res. Discl., 236, 380 (Ger), 1983) discloses a Mannich reaction of 1-naphthol with formalin and piperidine or morpholine to yield 2-(piperidinomethyl)-1-naphthol or 2-(morpholinomethyl)-1-naphthol, respectively. These compounds were subjected to hydrogenolysis (Pd/C) whereby 2-methyl-1-naphthol was produced Sibi et al (J. Org. Chem., 48 (11), 1935–1937, 1983) disclose reaction of 1-naphthol with diethyl carbamyl chloride in pyridine to produce a 1-naphthyl carbamate. Treatment of 1-naphthyl carbamate under the standard conditions for methylation of tertiary amides (1.1 equiv. sec-BuLi/TMEDA/THF/-78° C./1 hour) followed by Bis(dimethylamino)phosphoryl-1-naphthalene (2) was lithiated with sec-butyllithium in THF to give the ortho-lithiated species (3). Regioselective methylation was achieved by reacting naphthyl phosphorodiamidate (3) with methyl iodide to yield the compound of the structure (4) in 87% yield. Removal of the bis(dimethylamino)phosphoryl group with HCOOH/reflux/1 hour afforded 2-methyl-1-naphthol (1) in a yield of 87.6%.

Collet al (J. Org. Chem., 53 (22), 5345–5348, 1988) disclose process which may be illustrated as follows:

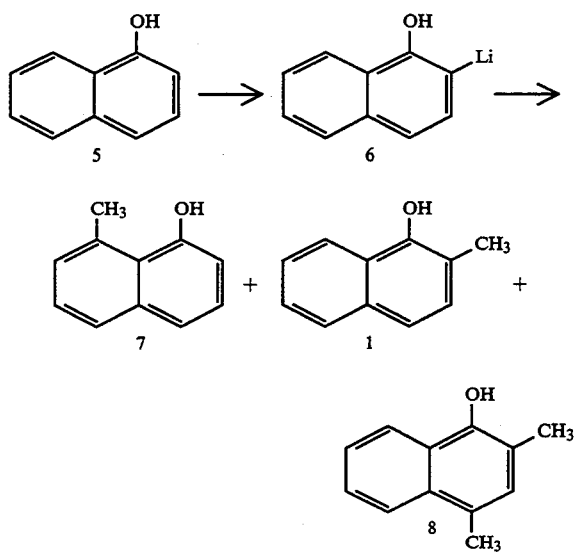

Direct lithiation of 1-naphthol (5) in anhydrous tetrahydropyran afforded 2-lithium-1-naphthol (6). The reaction was then quenched with methyl iodide. The usual extractive work up resulted in a mixture containing two monomethyl derivatives (7 and 1) and one dimethyl derivative (8) as well as the starting material (5) in a ratio of 2:10:1:7, respectively.

Rao et al (Indian J. Chem., Sect. B, 24B(3), 233–235, 1985) disclose the following depicted synthesis:

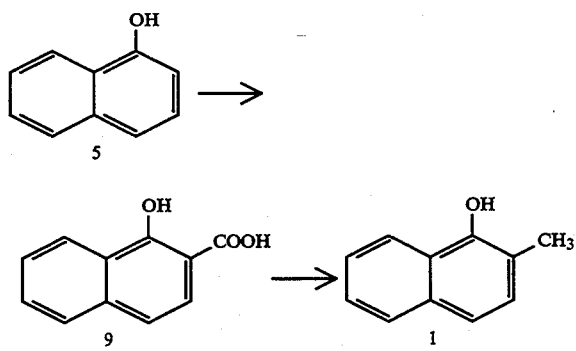

2-Methyl-1-naphthol (1) may be depicted as follows:

quenching with methyl iodide, warming to room temperature (8 to 12 hours) and NH₄Cl work-up, afforded 2-methyl-1-naphthyl carbamate in a yield of 90%. Carbamate removal was effected in a yield of 90% by reduction (LAH/THF/reflux;H⁺) or hydrolysis (NaOH/aqueous CH₃OH or HO(CH₂)₂OH/reflux) to yield 2-methyl-1-naphthol.

Saidi (Indian J. Chem., Sect. B. 21B(5), 474, 1982) teach the following reaction: n-Butyllithium (in hexane) was added to a solution of 1-naphthol (in dry benzene) under a nitrogen atmosphere. The solution was refluxed for another 3 hours to afford 2-lithium-1-naphthol. The alkylating agent, dimethyl sulfate, was added whereby a crude alkyl naphthol was produced. The crude residue contained 22% 2-methyl-1-naphthol, 67% 1-methoxynaphthalene and 6% 2-methyl-1-methoxynaphthalene.

Minami et al (Chem. Pharm. Bull., 27(3), 816–820, 1979) disclose the following reaction scheme: ethyl chloroformate was added, at a temperature of 0°–5° C. and over a period of 1 hour, to a solution of 1-hydroxy-2-naphthoic acid and triethylamine in tetrahydrofuran whereby the correspondence carbamate was produced. The reaction mixture was added to a solution of sodium borohydride in water, with stirring, at a temperature of 5° to 15° C., and over a period of 1 hour. Extraction with ether gave 2-methyl-1-naphthol in a yield of 69.2%.

Leach et al (U.S. Pat. No. 3,993.701) disclose the following synthetic process: methylation of 1-naphthol to 2-methyl-1-naphthol by CH₃OH, at 340° C. to 355° C. was catalyzed by Al₂O₃. The mixture so produced contained 2-methyl-1-naphthol in a yield of 32.3 to 40.7% and 1-naphthol in a yield of 50.67 to 61.1%.

Tasaka et al (JP 50047958) disclose the following reaction scheme: methylation of alpha-naphthol at position 2 was effected by vapor phase methylation of 1-naphthol at elevated temperature in the presence of catalyst comprising CeO₂ and Sb₂O₃, GeO₂, SnO₂ or MgO. Aqueous ammonia (28%) was added to a mixture of SnCl₄ and Ce(NO₃)₄·2NH₄NO₃·2H₂O in water at 50° C. The resulting precipitate was dried, calcinated for 3 hours at 600° C., and crushed to form a catalyst. 1-Naphthol/methanol mixture (1:6 molar) was passed over the catalyst at 425° C. and 1000 hr⁻¹ space velocity to give 72.5 wt. % 2-methyl-1-naphthol, 2.6 wt. % 4-methyl-naphthol and 2.2 wt. % of other material.

Inoue et al (Chem. Pharm. Bull., 24 (9), 2199–2203, 1976) disclose ferric oxide and chromium oxide to be new alkylating catalyst of phenols. The activity and selectivity of these oxide catalysts were examined by liquid-phase reaction. 1-Naphthol, methanol and ferric oxide were charged in an autoclave equipped with a magnetic stirrer. After air in the autoclave was replaced by hydrogen, the temperature was raised to 400° C. over a period of 45 to 50 minutes. At such temperature, the pressure reached 100 atm. After 3 hours, 2-methyl-1-naphthol was produced in a conversion of 57.6 mol %. The remainder was starting material.

Brown (Bull. Natl. Inst. Sci. India, No. 31, 167–178, 1965) discloses the following reaction scheme: Mannich reaction of 1-naphthol with piperidine and formaldehyde afforded 2-(piperidinomethyl)-1-naphthol in a yield of 45%. Reduction of 2-(piperidinomethyl)-1-naphthol in the presence of H₂/Pd/SrCO₃ afforded 2-methyl-1-naphthol in a yield of 85%.

Schleigh et al (Res. Discl., 129, 27–30, 1975) disclose the following synthetic process: hydrogenation of 2-morpholinomethyl-1-naphthol with 10% pd/c at the pressure of 62 psi gave 2-methyl-1-naphthol in 65% yield.

As is evident from the preceding review of the prior art, numerous processes are known for the synthesis of 2-methyl-1-naphthol, however, they all suffer from one or more of the following disadvantages:

The overall yield of 2-methyl-1-naphthol is generally low, mainly because of the formation of multiple products.

Starting materials and reagents are not readily available.

The reaction requires either anhydrous conditions, very high temperature (>200° C.) or very low temperature (−100° C.).

The Anon. (USA) Res. Discl. Publication gives no details of the process disclosed. The processes of Schleigh et al and Brown are disadvantageous as they give low yields of 2-methyl-1-naphthol (1).

The major disadvantage of prior art processes similar to the process of the present invention is that the Mannich reaction results in the production of the di-substituted Mannich base. Initially the Mannich reaction of 1-naphthol occurs predominantly at the C-2 position. The initial Mannich base produced becomes a more active substrate for the Mannich reaction. Consequently, the 1,4 di-substituted product is produced as a by-product. Moreover, hydrogenation of the Mannich base generates organic base (such as morphorine, piperidine or pyrrolidine). The organic base causes air oxidation during work-up. This makes it very difficult to obtain a clean final product and a purification step is invariably required.

The present invention overcomes this disadvantage through the use of 4-halo-1-naphthol. Since the C-4 position of 1-naphthol is blocked by a halogen atom (Cl, Br or I, preferably Cl) the Mannich reaction takes place only at the C-2 position. The presence of a halogen atom at the C-4 position provides yet another advantage.

The halide acid produced during the reduction of the Mannich base neutralizes generated organic base, such as dimethylamine. Upon completion of the reaction, the reaction mixture is neutral. As a result, air oxidation, which would otherwise occur during work-up, is prevented.

A second advantage is that the two-step procedure can be carried out in one pot. After the Mannich reaction of 1-naphthol with dimethylamine and formaldehyde, the reaction mixture can be subjected to direct hydrogenation.

The process of the present invention for preparing 2-methyl-1-naphthol (I) has several advantages over prior art processes.

The overall yield of 2-methyl-1-naphthol (1) is very high.

No purification step is required.

The starting material and reagents are readily available.

The process can be practiced in one step or in two steps.

No special precautions are required to carry out the reaction.

The process of the present invention for synthesis of 2-methyl-1-naphthol is illustrated by the following reaction scheme:

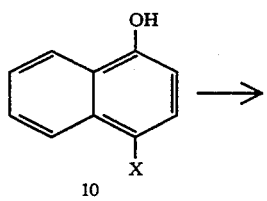

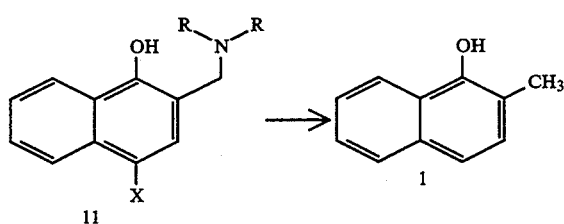

The Mannich reaction of 4-halo-1-naphthol (10, wherein X=Cl, Br or I) with aqueous formaldehyde and a secondary amine (NRR wherein R is methyl, ethyl or R and R together with nitrogen to which they are attached are combined to form a cyclic structure containing 4 to 5 carbon atoms, the cyclic structure optionally containing an oxygen ring member), such as dimethylamine, diethylamine, pyrrolidine, morphorine and piperidine, in water or aqueous alcohol (e.g. lnethanol or ethanol), is carried out to produce the Mannich base (11, wherein R and X are as previously defined). The reaction can be performed at room temperature or at a temperature above or below room temperature. The bimolecular aromatic Mannich reaction has been detailed by Heaney (see Comprehensive Organic Synthesis, edited by B. M. Trost and I. Fleming, Pergamon Press, New York, 1991, Vol.2, p 953–973).

The Mannich base (11) is reduced by catalytic hydrogenation or catalytic transfer hydrogenation to produce 2-methyl-1-naphthol. The catalytic hydrogenation may be effected in any conventional manner so long as the process employed enables cleavage of the secondary amine and removal of the halogen atom. Preferably, the process is carried out at a temperature of from room temperature to 100° C. and under a hydrogen pressure of from atmospheric pressure to 60 psi. Any suitable hydrogenation catalyst, such as palladium or platinum, may be employed. The preferred catalyst is palladium supported on carbon. More preferably, it is a palladium on carbon catalyst containing 3 to 10% palladium.

The catalytic transfer hydrogenation has been detailed by Johnstone and Wilby (See Chem. Rev., 1985, 129–170). Suitable hydrogen donors are hydrazine, formic acid, formate, phosphinic acid, phosphinate, indoline, cyclohexene, and cyclohexadiene. The preferred catalyst is palladium on carbon containing 3 to 10% palladium.

When the reaction is complete, the catalyst is removed and the filtrate is concentrated. The residue is taken up in an organic solvent (such as ethyl acetate, ether or dichloromethane), washed with water or brine and dried. Evaporation of the organic solvent affords 2-methyl-1-naphthol.

The following examples are offered merely to illustrate the process of the invention. They are not intended as limitations thereof.

EXAMPLE 1

To illustrate tile 2-step one pot process of the present invention the following procedure was carried out:

A mixture of 17.90 g (100 m mole) 4-chloro-1-naphthol (12), 10.02 g of 37% formaldehyde and 16.91 g (150 m mole) of 40% dimethylamine, in 200 ml ethanol, was stirred at room temperature for 1 hour. 1.79 g of 10% Pd-C were added to the reaction mixture. The reaction mixture was then hydrogenated at 50 psi hydrogen for 17 hours. After a standard work-up (as described in the 2-step process of Example 2 which follows) 2-methyl-1-naphthol was obtained in a yield of 97.5%.

EXAMPLE 2

To illustrate the 2-step process of the present invention the following procedures were carried out:

A. Preparation of 4-chloro-2-(dimethylaminomethyl)-1-naphthol (13)

The Mannich reaction of 17.90 g (100 m mole) 4-chloro-1-naphthol (12) with 10.02 g (123 mmole) 37% formaldehyde and 16.91 g (150 m mole) 40% dimethylamine was carried out under stirring, in 200 ml ethanol, at room temperature, for a period of 1 hour. The reaction mixture was poured over 300 g crushed ice. The resulting precipitate was collected, washed with ice water, and dried under vacuum to give 23.45 g (representing a yield of 99.5%) 4-chloro-2-(dimethylaminomethyl)-1-naphthol (13): $^1$H NMR (300 MHz, DMSO-$d_6$) δ 2.29 (s, 6H), 3.78 (s, 2H), 7.34 (s, 1H), 7.40 (bs, 1H, exch. with $D_2O$), 7.50–7.62 (m, 2H), 8.01 (d, 1H, J=8 Hz), 8.16 (d, 1H, J=8 Hz); mass spectrum, m/z 235 (M+).

B. Preparation of 2-methyl-1-naphthol (1)

A mixture of 14.18 g (60 m mole) 4-chloro-2-(dimethylaminomethyl)-1-naphthol (13) and 1.43 g 10% Pd-C in 240 ml ethanol was hydrogenated at 50 psi hydrogen atmosphere for 17 hours at room temperature then filtered over a layer of Celite. The filtrate was concentrated under reduced pressure. The residue was partitioned between water and ethyl acetate. The organic layer was washed with water and brine, dried over anhydrous sodium sulfate and evaporated, whereby 8.99 g (representing a yield of 95%) 2-methyl-1-naphthol (1) were obtained: $^1$H NMR (300 MHz, DMSO-$d_6$) δ2.32 (s, 3H), 7.21–7.40 (m, 4H), 7.75 (d, 1H, J=8 Hz), 8.15 (d, 1H, J=8 Hz), 9.01 (s, 1H, exch. with $D_2O$); m/z 158 (M+).

The process of the present invention is illustrated by the following reaction scheme:

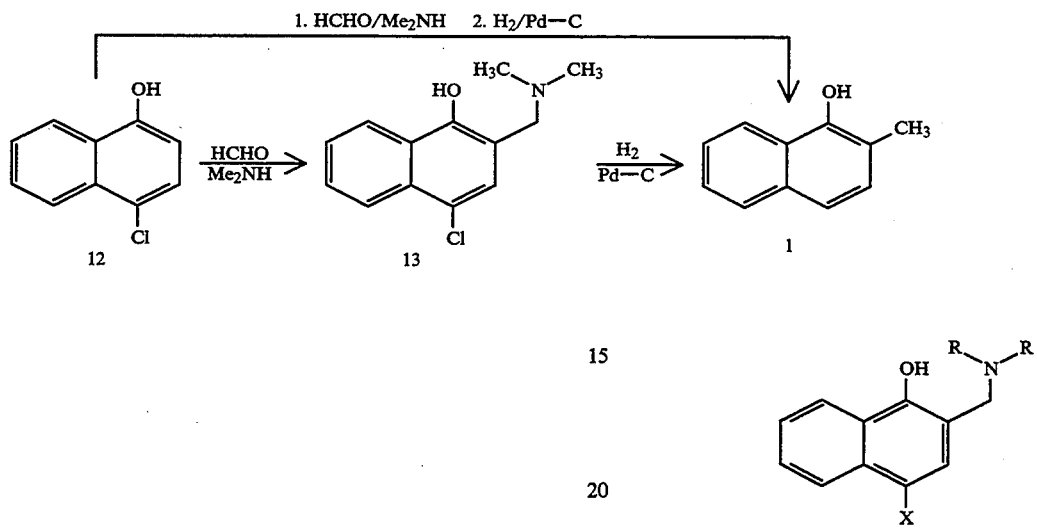

We claim:

1. Process for preparing 2-methyl-1-naphthol comprising reacting a compound of the formula wherein X is Cl, Br or I with formaldehyde and a secondary amine of the formula wherein R is methyl, ethyl or R and R together with the nitrogen to which they are attached are combined to form a cyclic structure containing 4 to 5 carbon atoms or a cyclic structure containing 4 to 5 carbon atoms an oxygen atom to produce a reaction mixture containing a Mannich base of the formula wherein R and X are as previously defined, then hydrogenating said Mannich base to produce said 2-methyl-1-naphthol.

2. The process as claimed in claim 1, wherein X is chlorine and the secondary amine is dimethylamine.

3. The process according to claim 1, wherein said reacting and said hydrogenating are carried out in the same reaction vessel and without isolation of said Mannich base.

4. The process according to claim 1, wherein the Mannich base is isolated from said reaction mixture then subjected to said hydrogenating.

5. The process according to claim 4, wherein said Mannich base is isolated by pouring said reaction mixture over ice, collecting resulting precipitate and washing the collected precipitate with ice water.

6. The process according to claim 2, wherein said reacting and said hydrogenating are carried out in the same reaction vessel and without isolation of said Mannich base.

7. The process according to claim 2, wherein the Mannich base is isolated from said reaction mixture then subjected to said hydrogenating.

8. The process according to claim 7, wherein the Mannich base is isolated by pouring said reaction mixture over ice, collecting resulting precipitate and washing the collected precipitate with ice water.

9. The process according to claim 1, wherein said reacting is carried out in a lower alkanol reaction medium.

10. The process according to claim 1, wherein said hydrogenating is carried out in the presence of Pd-C catalyst.

* * * * *

UNITED STATES PATENT AND TRADEMARK OFFICE
CERTIFICATE OF CORRECTION

PATENT NO. : 5,420,362
DATED : May 30, 1995
INVENTOR(S) : Mu-Ill Lim, Linas Stasaitis, Yuo-Guo Pan and Alexander Chan It is certified that error appears in the above-indentified patent and that said Letters Patent is hereby corrected as shown below:

At Column 1, line 15 delete "Collet al" and insert --Coll et al--.

Remove text in Column 1, beginning with the line immediately beneath the title "Synthesis of 2-Methyl-1-Naphthol" through line 65 of Column 1 and insert the removed text into Column 2, immediately below the depicted structures and immediately above line 48 which reads "1-naphthol (5) was heated with twice its weight of".

Signed and Sealed this

Fifteenth Day of August, 1995

Attest:

BRUCE LEHMAN

Attesting Officer

Commissioner of Patents and Trademarks